United States Patent
Geiger et al.

(10) Patent No.: US 7,822,461 B2
(45) Date of Patent: Oct. 26, 2010

(54) SYSTEM AND METHOD FOR ENDOSCOPIC PATH PLANNING

(75) Inventors: Bernhard Geiger, Cranbury, NJ (US); Atilla Peter Kiraly, Plainsboro, NJ (US); David P. Naidich, New York, NY (US); Carol L. Novak, Newtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 943 days.

(21) Appl. No.: 10/888,368

(22) Filed: Jul. 9, 2004

(65) Prior Publication Data

US 2005/0107679 A1    May 19, 2005

Related U.S. Application Data

(60) Provisional application No. 60/486,319, filed on Jul. 11, 2003.

(51) Int. Cl.
*A61B 5/05* (2006.01)

(52) U.S. Cl. .............. 600/415; 600/109; 600/112; 600/117; 600/416; 600/420; 606/45

(58) Field of Classification Search ........... 600/117, 600/407, 424, 427, 109, 112, 118, 101, 410, 600/411, 415, 416, 420, 425, 437; 606/45
See application file for complete search history.

(56) References Cited

U.S. PATENT DOCUMENTS

| | | | | |
|---|---|---|---|---|
| 5,365,927 A | * | 11/1994 | Roemer et al. | 600/410 |
| 5,458,111 A | * | 10/1995 | Coin | 600/560 |
| 5,611,025 A | * | 3/1997 | Lorensen et al. | 345/419 |
| 5,699,799 A | * | 12/1997 | Xu et al. | 600/407 |
| 5,971,767 A | * | 10/1999 | Kaufman et al. | 434/267 |
| 6,343,936 B1 | * | 2/2002 | Kaufman et al. | 434/262 |
| 6,346,940 B1 | * | 2/2002 | Fukunaga | 345/427 |
| 6,694,163 B1 | * | 2/2004 | Vining | 600/407 |
| 6,702,736 B2 | * | 3/2004 | Chen et al. | 600/117 |
| 6,892,090 B2 | * | 5/2005 | Verard et al. | 600/424 |
| 7,167,180 B1 | * | 1/2007 | Shibolet | 345/474 |
| 7,194,117 B2 | * | 3/2007 | Kaufman et al. | 382/128 |
| 2003/0032876 A1 | * | 2/2003 | Chen et al. | 600/407 |
| 2004/0015070 A1 | * | 1/2004 | Liang et al. | 600/407 |

OTHER PUBLICATIONS

D. Mayer, D. Bartz, S. Ley, S. Thust, C. Heussel, H. Kauczor and W. StraBer: "Segmentation and Virtual Exploration of Tracheobronchial Trees"; Computer Aided Radiology and Surgery; Jun. 2003; Elsevier, pp. 35-40.

(Continued)

*Primary Examiner*—Brian Casler
*Assistant Examiner*—Joel M Lamprecht
(74) *Attorney, Agent, or Firm*—Donald B. Paschburg; F. Chau & Associates, LLC (57) ABSTRACT

A system and method for endoscopic path planning is provided. The method comprises: identifying a target in a lung, wherein the target is located in a peripheral airway of the lung; generating an endoscopic path to the target, wherein a peripheral artery is used as a surrogate for the peripheral airway; and viewing the endoscopic path.

11 Claims, 8 Drawing Sheets

OTHER PUBLICATIONS

Kiraly, Higgins, McLennan, Hoffman, Reinhardt: "Three—dimensional human airway segmentation methods for Clinical virtual bronchoscopy" Academic Radiology, vol. 9, No. 10, Sep. 2002, pp. 1153-1168, XP002330892 Elsevier p. 1154, left—hand column—p. 1155, left—hand column p. 1162, right—hand column—p. 1165, left—hand column figures 9, 10.

Sonka, Park, Hoffman: "Validation of an enhanced knowledge—based method for segmentation and quantitative analysis of intrathoracic airway trees—dimensional CT images" Proc. SPIE, Medical Imaging 1995 Physiology and Function from Multi-dimensional Images, vol. 2433, May 1995, pp. 158-166, XP002330897 p. 159, paragraph 2—p. 160, paragraph 2.5.

Park W et al: "Segmentation of Airway Trees: A Fuzzy Logic Intrathoracic Approach" IEEE Transactionson Medical Imaging, IEEE Inc. New York, US, vol. 17, No. 4, Aug. 1998 pp. 489-497, XP000787273 ISSN: 0278-0062 p. 490, left—hand column, paragraph II—p. 493, left—hand column figure 1.

Higgins W E et al: "Virtual Bronschoscopy for Three—Dimensional Pulmonary Image Assessment: State of the Art and Future Needs" Radiographics, Radiological Society of North America, Oak Brook,, US, vol. 3, No. 18, May 1998, pp. 761-778, XP008002476 ISSN: 0271-5333 p. 762, left—hand column—p. 763, right—hand column p. 764, right—hand column—p. 765, left—hand column p. 770, right—hand column p. 774, left—hand column.

Paik David S et al: "Automated flight path planning for virtual endoscopy" Medical Physics, American Institute of Physics. New York, US, vol. 25, No. 5, May 1998, pp. 629-637, XP012010458 ISSN: 0094-2405 p. 629, left'hand column p. 631, left—hand p. 634, left—hand column—p. 630, column paragraph IV—column, paragraph V.

Deschamps T et al: "Fast extraction of minimal paths in 3D images and applications to virtual endoscopy" Medical Image Analysis, Oxford University Press, Oxofrd, GB, vol. 5, 2001, pp. 281-299, XP002904305 ISSN: 1361-8415 p. 1.

* cited by examiner

SYSTEM AND METHOD FOR ENDOSCOPIC PATH PLANNING

CROSS-REFERENCE TO RELATED APPLICATIONS

This application claims the benefit of U.S. Provisional Application No. 60/486,319, filed Jul. 11, 2003, a copy of which is herein incorporated by reference.

BACKGROUND OF THE INVENTION

1. Technical Field

The present invention relates to endoscopic path planning, and more particularly, to endoscopic path planning using arteries as a surrogate for airways.

2. Discussion of the Related Art

Bronchoscopy with transbronchial biopsy (TBBx) is a diagnostic procedure in which a bronchoscope is inserted through the nose or mouth to collect multiple specimens of lung tissue. TBBx has been shown to be less traumatic to patients as compared to other methods of biopsying suspicious lung nodules, such as transthoracic needle biopsy (TTNBx) and video assisted thorascopic surgery (VATS). Until recently, however, TBBx has been limited to central nodules located close to major airways due to the size of the bronchoscope.

With the introduction of ultra-thin bronchoscopes, it is now possible to traverse peripheral airways to reach peripheral nodules in the lung. It is difficult, however, to plan a path through numerous branching airways to reach desired peripheral nodules. Even when using multi-slice computed tomography (CT) imaging systems capable of obtaining image volumes with an isotropic resolution of, for example, 0.5 mm, peripheral airways near the desired nodule may not be visible in the image data due to partial volume effects. Further, as airways branch repeatedly into smaller peripheral airways, the number of possible pathways increases exponentially, making it difficult to plan a pathway to a desired peripheral nodule.

Virtual endoscopy is a technique used to create visualizations from three-dimensional (3D) medical image scans that have a similar appearance to the images produced by current endoscopic procedures such as a bronchoscopy, angioscopy, and colonoscopy. These virtual endoscopic visualizations are a valuable aid to medical experts by showing them the path they will be traveling along during an actual bronchoscopy. However, virtual endoscopic techniques are limited by the resolution of the available 3D data, and are thus confined to central airways of the lung that are visible in the CT image data.

It has been shown that peripheral arteries are more visible than peripheral airways in CT image data because they do not suffer from the same degree of partial volume effects. In addition, it has been demonstrated in anatomic studies that airways and arteries parallel each other throughout the lung.

Accordingly, there is a need for a system and method for virtual endoscopic path planning that enables a medical expert such as a bronchoscopist to plan a path through numerous peripheral airways to reach desired peripheral nodules in a lung.

SUMMARY OF THE INVENTION

The present invention overcomes the foregoing and other problems encountered in the known teachings by providing a system and method for endoscopic path planning using arteries as a surrogate for airways.

In one embodiment of the present invention, a method for endoscopic path planning comprises: identifying a target in a lung, wherein the target is located in a peripheral airway of the lung; and generating an endoscopic path to the target, wherein a peripheral artery is used as a surrogate for the peripheral airway. The target is one of a nodule, cancerous protrusion, non-cancerous protrusion, lesion, tumor, and stenosis.

The method further comprises: acquiring data associated with the lung. The data is acquired by one of a computed tomographic (CT), helical CT, x-ray, positron emission tomographic, fluoroscopic, ultrasound, and magnetic resonance (MR) imaging technique. The step of identifying the target comprises one of manually selecting the target from the lung and automatically selecting the target from the lung.

The step of generating an endoscopic path to the target comprises: segmenting data associated with the lung, wherein airways and arteries of the lung are segmented; computing an airway tree of the segmented airways and an artery tree of the segmented arteries; matching the computed airway and artery trees; determining the endoscopic path to the target; and selecting a jump location where the endoscopic path switches to the peripheral artery. The jump location is near an end of a detectable peripheral airway and a corresponding location along the peripheral artery. The jump location is at a midpoint of a branch in a detectable peripheral airway and a corresponding location along the peripheral artery.

The step of generating an endoscopic path to the target comprises: segmenting data associated with the lung, wherein airways and arteries of the lung are segmented; computing an airway tree of the segmented airways and an artery tree of the segmented arteries; selecting an artery path that leads to the target; selecting an airway path that matches the artery path; and selecting a jump location where the endoscopic path switches to the peripheral artery. The method further comprises viewing the endoscopic path.

In another embodiment of the present invention, a method for endoscopic path planning comprises: manually selecting a target in a lung, wherein the target is located in or near a peripheral airway of the lung; manually selecting a location inside an artery leading to the target, and a location inside an airway leading to the target, wherein the two locations form a jump point; automatically determining which of the two locations corresponds to the inside of the artery and the inside of the airway; manually selecting a target point within an artery that is near the target; automatically generating a retrograde angioscopic path from the target point to the jump point; and automatically generating a retrograde bronchoscopic path from the jump point to a trachea.

The method further comprises: manually navigating along the retrograde angioscopic path from the target to the jump point; automatically determining that the retrograde angioscopic path has reached the jump point when a virtual endoscope traveling along the retrograde angioscopic path is within a threshold distance of the jump point; and automatically generating a forward path from the trachea to the target by reversing the retrograde angioscopic and bronchoscopic paths.

In yet another embodiment of the present invention, a method for endoscopic path planning comprises: manually selecting a target in a lung; manually selecting a location inside an artery leading to the target, and a location inside an airway parallel to the selected artery, wherein the two locations form a jump point; manually selecting a point within an artery that is near the target; manually generating a retrograde angioscopic path from the artery near the target to the jump point; and manually generating a retrograde bronchoscopic path from the jump point to a trachea. The method further comprises automatically generating a forward path from the trachea to the target by reversing the retrograde angioscopic and bronchoscopic paths.

In another embodiment of the present invention, a method for performing a bronchoscopy using a planned endoscopic path comprises: inserting a bronchoscope into a lung; acquiring a first image, wherein the first image includes a location of a tip of the bronchoscope in the lung; registering the first image with a corresponding image from the planned endoscopic path; and determining where the tip of the bronchoscope is located in relation to where it is located in the planned endoscopic path. The method further comprises adjusting the location of the tip of the bronchoscope to match its location in the planned endoscopic path.

In yet another embodiment of the present invention, a system for endoscopic path planning comprises: a memory device for storing a program; a processor in communication with the memory device, the processor operative with the program to: identify a target in a lung, wherein the target is located in or near a peripheral airway of the lung; and generate an endoscopic path to the target, wherein a peripheral artery is used as a surrogate for the peripheral airway. The target is one of a nodule, cancerous protrusion, non-cancerous protrusion, lesion, tumor, and stenosis.

The processor is further operative with the program code to acquire data associated with the lung. The data is acquired by one of a computed tomographic (CT), helical CT, x-ray, positron emission tomographic, fluoroscopic, ultrasound, and magnetic resonance (MR) imaging technique. The processor is further operative with the program code when identifying the target to select the target from the lung.

The processor is further operative with the program code when generating an endoscopic path to the target to: segment data associated with the lung, wherein airways and arteries of the lung are segmented; compute an airway tree of the segmented airways and an artery tree of the segmented arteries; match the computed airway and artery trees; determine the endoscopic path to the target; and select a jump location where the endoscopic path switches to the peripheral artery. The jump location is near an end of a detectable peripheral airway and a corresponding location along the peripheral artery. The jump location is at a midpoint of a branch in a detectable peripheral airway and a corresponding location along the peripheral artery.

The processor is further operative with the program code when generating an endoscopic path to the target to: segment data associated with the lung, wherein airways and arteries of the lung are segmented; compute an airway tree of the segmented airways and an artery tree of the segmented arteries; select an artery path that leads to the target; select a matching bronchial path; and select a jump location where the endoscopic path switches to the peripheral artery; and display the endoscopic path.

In another embodiment of the present invention, a computer program product comprising a computer useable medium having computer program logic recorded thereon for endoscopic path planning, the computer program logic comprises: program code for identifying a target in a lung, wherein the target is located in a peripheral airway of the lung; and program code for generating an endoscopic path to the target, wherein a peripheral artery is used as a surrogate for the peripheral airway.

In another embodiment of the present invention, a system for endoscopic path planning comprises: means for identifying a target in a lung, wherein the target is located in a peripheral airway of the lung; and means for generating an endoscopic path to the target, wherein a peripheral artery is used as a surrogate for the peripheral airway.

In yet another embodiment of the present invention, a method for automatically deriving computer-generated virtual endoscopic pathways leading from airways to peripheral nodules using arteries as substitute markers for the location of peripheral airways when the peripheral airways are not detectable by computed tomographic (CT) scans comprises: identifying a nodule in a lung, wherein the nodule is located in or near one of the peripheral airways; generating a virtual endoscopic path to the nodule, wherein one of the peripheral arteries is used as a substitute for one of the peripheral airways leading to the nodule, the step of generating the virtual endoscopic path comprises: segmenting data associated with the lung, wherein airways and arteries of the lung are segmented; computing an airway tree of the segmented airways and an artery tree of the segmented arteries; matching the computed airway and artery trees; determining the virtual endoscopic path to the target; and selecting a jump location where the virtual endoscopic path switches to the peripheral artery which is the substitute for one of the peripheral airways; and viewing the virtual endoscopic path.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Figure 1:
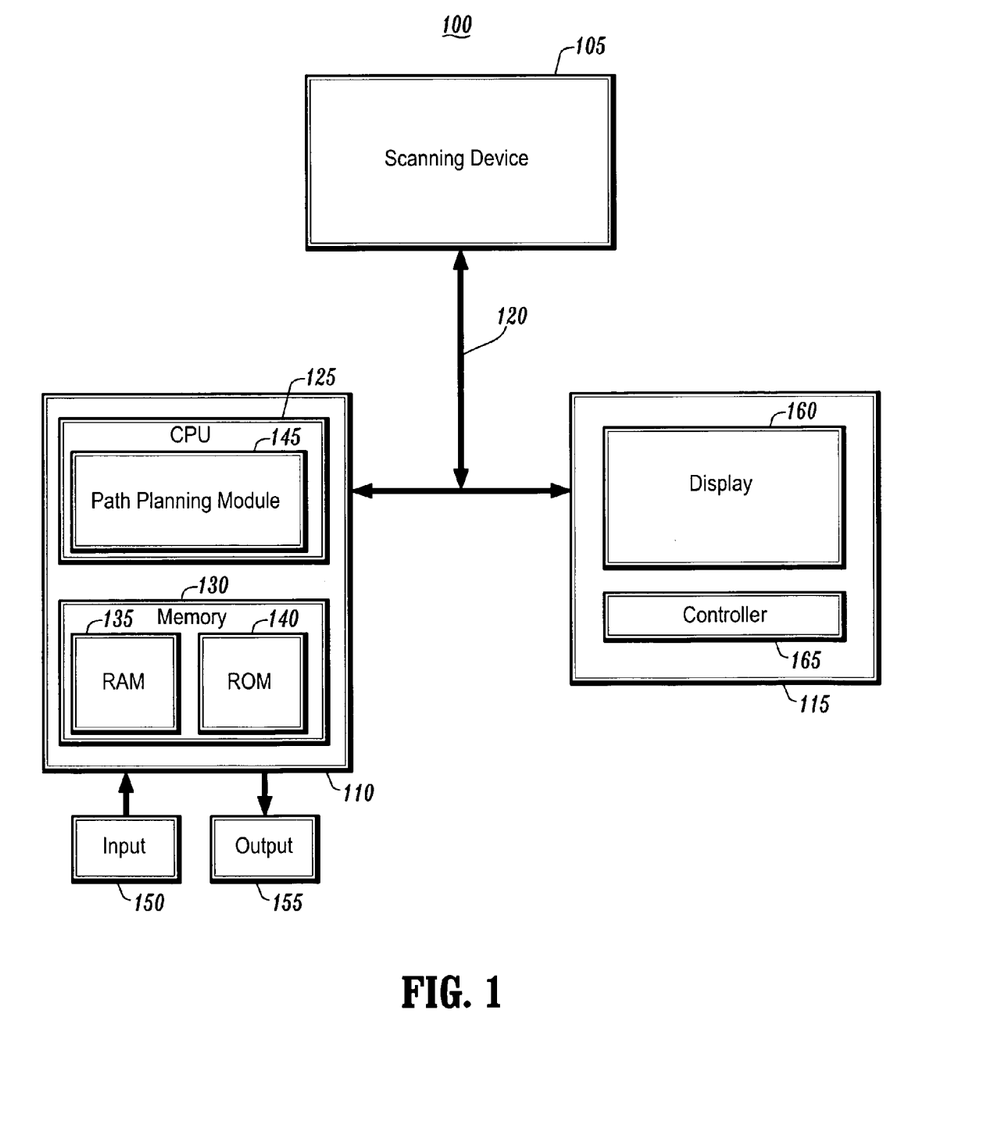
FIG. 1 is a block diagram of a system for endoscopic path planning according to an exemplary embodiment of the present invention.

FIG. 1 is a block diagram of a system 100 for endoscopic path planning according to an exemplary embodiment of the present invention. As shown in FIG. 1, the system 100 includes, inter alia, a scanning device 105, a personal computer (PC) 110 and an operator's console and/or virtual navigation terminal 115 connected over, for example, an Ethernet network 120. The scanning device 105 may be a magnetic resonance imaging (MRI) device, a computed tomography (CT) imaging device, a helical CT device, a positron emission tomography (PET) device, a two-dimensional (2D) or three-dimensional (3D) fluoroscopic imaging device, a 2D, 3D, or four-dimensional (4D) ultrasound imaging device, or an x-ray device, etc.

The PC 110, which may be a portable or laptop computer, a personal digital assistant (PDA), etc., includes a central processing unit (CPU) 125 and a memory 130, which are connected to an input 150 and an output 155. The CPU 125 includes a path planning module 145 that includes one or more methods for planning endoscopic paths using arteries as a surrogate for airways. The CPU 125 may also include a diagnostic module, which is used to perform automated diagnostic or evaluation functions of medical image data. In addition, the CPU 125 may further be coupled to or include a volume of interest (VOI) selector and a lung volume examination device.

The memory 130 includes a random access memory (RAM) 135 and a read only memory (ROM) 140. The memory 130 can also include a database, disk drive, tape drive, etc., or a combination thereof. The RAM 135 functions as a data memory that stores data used during execution of a program in the CPU 125 and is used as a work area. The ROM 140 functions as a program memory for storing a program executed in the CPU 125. The input 150 is constituted by a keyboard, mouse, etc., and the output 155 is constituted by a liquid crystal display (LCD), cathode ray tube (CRT) display, printer, etc.

The operation of the system 100 is controlled from the virtual navigation terminal 115, which includes a controller 165, for example, a keyboard, and a display 160, for example, a CRT display. The virtual navigation terminal 115 communicates with the PC 110 and the scanning device 105 so that 2D image data collected by the scanning device 105 can be rendered into 3D data by the PC 110 and viewed on the display 160. It is to be understood that the PC 110 can be configured to operate and display information provided by the scanning device 105 absent the virtual navigation terminal 115, using, for example, the input 150 and output 155 devices to execute certain tasks performed by the controller 165 and display 160.

The virtual navigation terminal 115 further includes any suitable image rendering system/tool/application that can process digital image data of an acquired image dataset (or portion thereof) to generate and display 2D and/or 3D images on the display 160. More specifically, the image rendering system may be an application that provides 2D/3D rendering and visualization of medical image data, and which executes on a general purpose or specific computer workstation. Moreover, the image rendering system enables a user to navigate through a 3D image or a plurality of 2D image slices. The PC 110 may also include an image rendering system/tool/application for processing digital image data of an acquired image dataset to generate and display 2D and/or 3D images.

As shown in FIG. 1, the path planning module 145 is also used by the PC 110 to receive and process digital medical image data, which as noted above, may be in the form of raw image data, 2D reconstructed data (e.g., axial slices), or 3D reconstructed data such as volumetric image data or multiplanar reformats, or any combination of such formats. The data processing results can be output from the PC 110 via the network 120 to an image rendering system in the virtual navigation terminal 115 for generating 2D and/or 3D renderings of image data in accordance with the data processing results, such as segmentation of organs or anatomical structures, color or intensity variations, and so forth.

It is to be understood that the system and method according to the present invention for endoscopic path planning may be implemented as extensions or alternatives to conventional endoscopic methods for processing and navigating through medical image data. Further, it is to be appreciated that exemplary systems and methods described herein can be readily implemented with 3D medical images and computer-aided diagnosis (CAD) systems or applications that are adapted for a wide range of imaging modalities (e.g., CT, MRI, etc.) and for diagnosing and evaluating various abnormal pulmonary structures or lesions such as lung nodules, tumors, stenoses, inflammatory regions, etc. In this regard, although exemplary embodiments may be described herein with reference to particular imaging modalities or particular anatomical features, nothing should be construed as limiting the scope of the invention.

It is to be further understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

Figure 2:
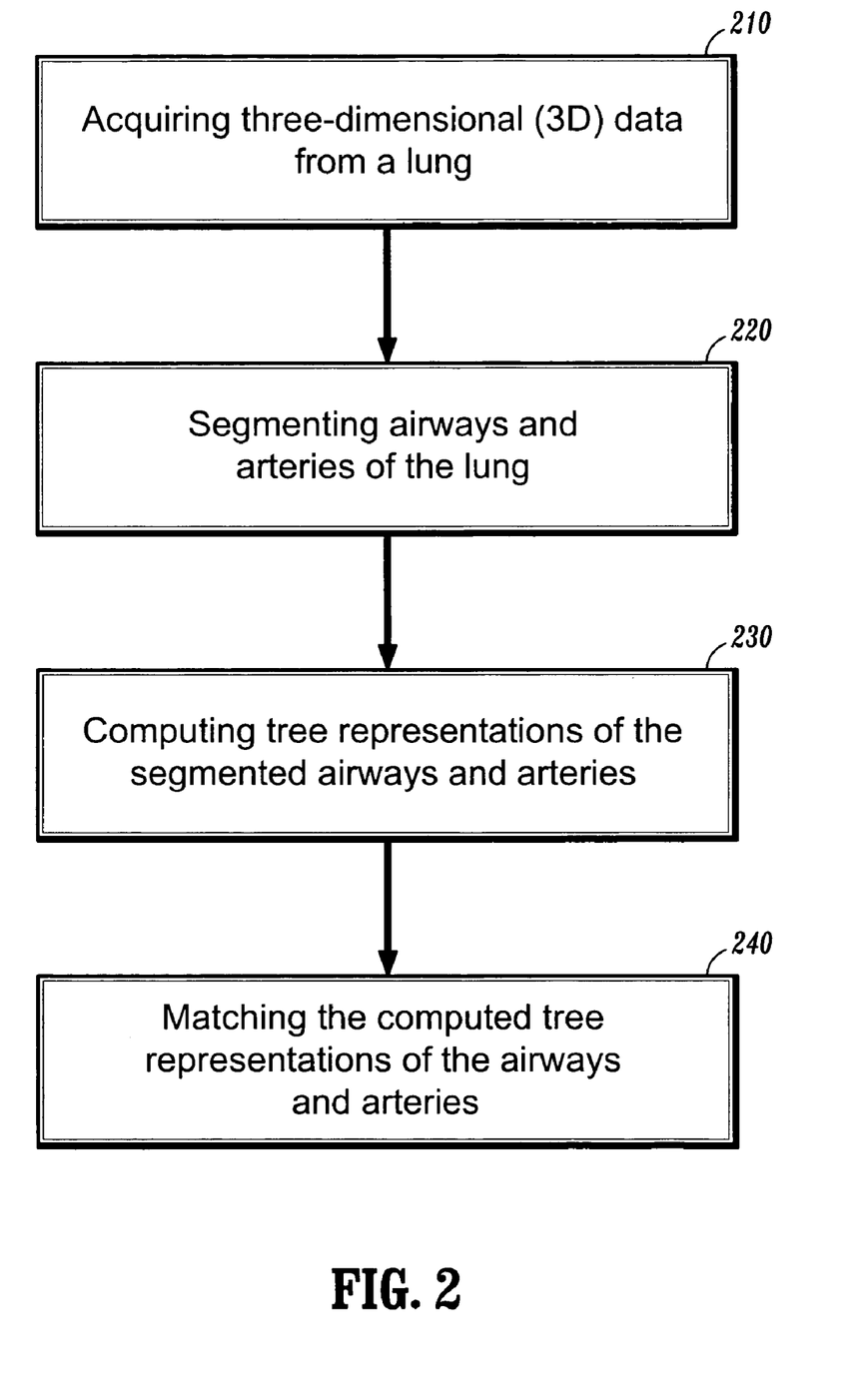
FIG. 2 is a flowchart illustrating a method for determining which arteries can be used as surrogates for airways according to an exemplary embodiment of the present invention.

FIG. 2 is a flowchart showing an operation of a method for determining which arteries can be used as surrogates for detectable and undetectable peripheral airways according to an exemplary embodiment of the present invention. As shown in FIG. 2, 3D data is acquired from a lung or pair of lungs (step 210). This is accomplished by using the scanning device 105, for example a CT scanner, to scan a lung thereby generating a series of 2D images associated with the lung. The 2D images of the lung may then be converted or transformed into a 3D rendered image.

After the 3D data is acquired from the lung, in one embodiment of the present invention, airways (e.g., bronchi) and arteries (e.g., blood vessels) in the lungs are automatically segmented (step 220). Several conventional techniques may be used to segment the airways and arteries in this step. One technique for airway segmentation is described in: Kiraly A. P., Higgins W. E., McLennan G., et al., "Three-dimensional human airway segmentation methods for clinical virtual bronchoscopy", Academic Radiology 9:1153-1168, 2002, a copy of which is herein incorporated by reference.

In one of the segmentation methods described by Kiraly et al., an automatic airway segmentation image $S_A$ is initially computed via adaptive region growing to segment the airways. In this method, a given root site $r_A$ is indicated at the proximal end of an airway tree within the CT image of the lung I. The root site $r_A$ may be manually selected, for example, by a user of the virtual navigation terminal 115 or automatically selected using image processing techniques for locating and selecting anatomical parts or portions thereof such as the trachea. One of the methods for automatic segmentation described by Kiraly et al. is composed of repeated 3D region growing iterations where each iteration uses a threshold T (initially −1000 HU) and the root site $r_A$ to determine a segmentation. An optimal threshold T is found by repeating this process with increasing values of the threshold T. Additional voxels are added to the segmentation as the threshold T is increased because all neighboring voxels with HU values below the threshold T become part of the segmentation.

Figure 4A:
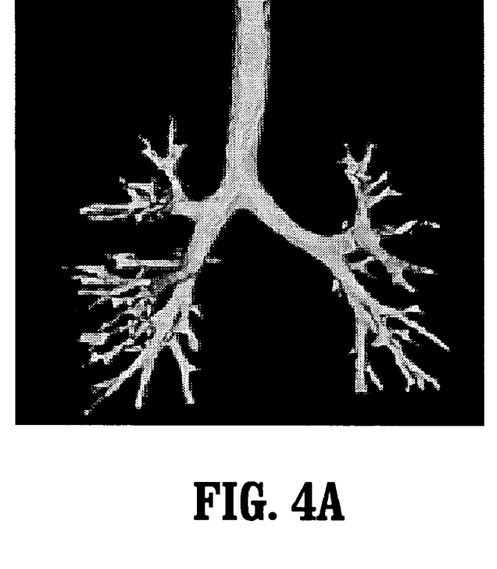
FIG. 4A is a segmented bronchial tree obtained using region growing.

In this method, it is assumed that the threshold T eventually reaches a point where it is high enough such that the region growing breaks through the bronchial wall and enters the parenchyma. Because the total volume V of the segmentation is computed each time 3D region growing is performed, this event can be detected by a sharp increase in the volume. The sharp increase is termed as an "explosion" and is determined by a preset value called the "explosion parameter" E. The region growing immediately prior to the detected explosion forms the segmentation image $S_A$. An example of a segmented bronchial tree obtained using the above described technique is shown in FIG. 4A.

Figure 4B:
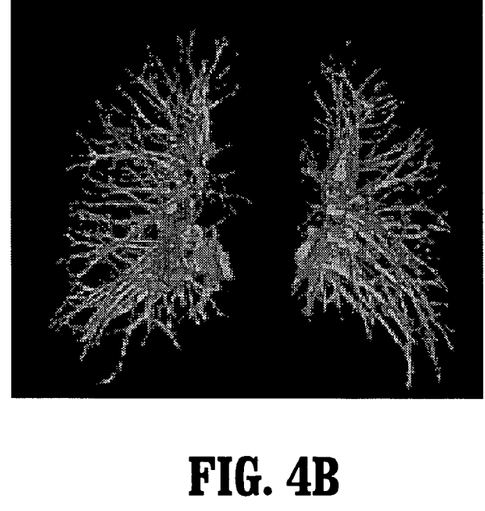
FIG. 4B is a segmented arterial tree obtained using region growing.

The arteries are automatically segmented in step 220 using, for example, a mask-limited threshold. An image of the segmented arteries $S_B$ is produced by a threshold $T_v$ of the original CT image. Any portion of the image with an HU value of $T_v$ or greater is included in the segmentation. Because the original CT image contains no contrast, this technique also segments portions of the heart. The extraneous portions of the original CT image are eliminated by masking the result with a lung mask. A standard region growing at the trachea with a threshold of −500 HU followed by a binary closing forms this mask. Because airway walls also tend to lie within the segmentation, most of these walls are deleted by subtracting dilated versions of the segmented airway images. The resulting image of the arteries achieves a more detailed segmentation as compared to those of the airways in peripheral regions because they do not suffer from the same degree of partial volume averaging as the bronchial wall. An example of a segmented arterial tree obtained using this technique is shown in FIG. 4B.

After the airways and arteries of the image are segmented, tree representations of the segmented airways and arteries are automatically computed (step 230). There are several methods by which the bronchial and arterial segmentations $S_A$ and $S_B$, may be used to compute a tree structure of the given segmentations $S_A$ and $S_B$, such as those described in: Kiraly A. P., Helferty J., Hoffman E. A., McLennan J., and Higgins W. E., "Analysis of branching tubular structures in 3D digital images", IEEE Transactions on Medical Imaging, to be published October 2004, a copy of which is herein incorporated by reference. The methods described by Kiraly et al. provide a variety of features, including smooth, sub-voxel paths, and quantitative direction vectors.

The tree computation, of step 230, starts with the skeletonization of the previously segmented bronchial airways and arteries and proceeds through several steps. The skeleton of the segmented image (either the airway segmentation $S_A$ or the artery segmentation $S_B$) is first computed using distance transforms to capture end-points followed by homotopy-preserving voxel elimination for thinning. Next, a raw tree structure is formed using the computed skeleton, although in many cases it may contain false branches. This tree structure describes the segmentation as a series of branches that are connected to each other. The tree structure and the segmented image are then used to measure certain criteria for the elimination of false branches. The remaining tree structure is then smoothed and centered. Viewing directions are then assigned to each point in the tree structure in order to allow an endoscopic rendering to be automatically generated. Examples of the computed tree representations of the segmented airways and arteries are shown in FIGS. 5A and 5B.

Figure 5A:
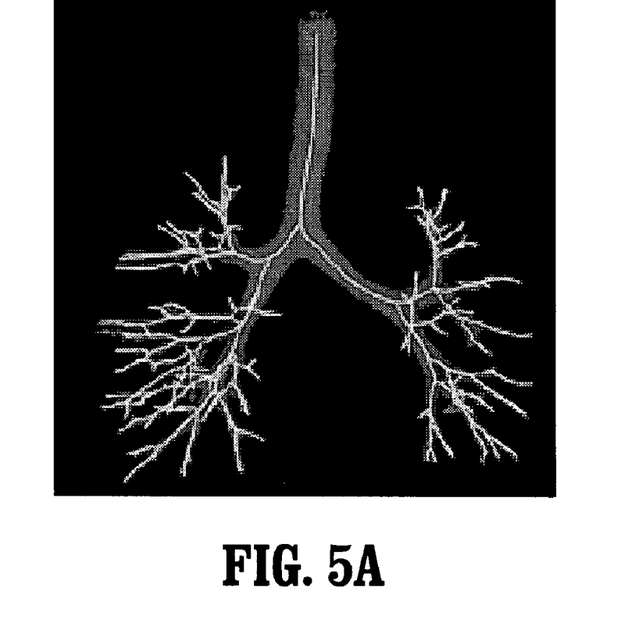
FIG. 5A is a computed bronchial tree model using the segmented bronchial tree of FIG. 4A.
Figure 5B:
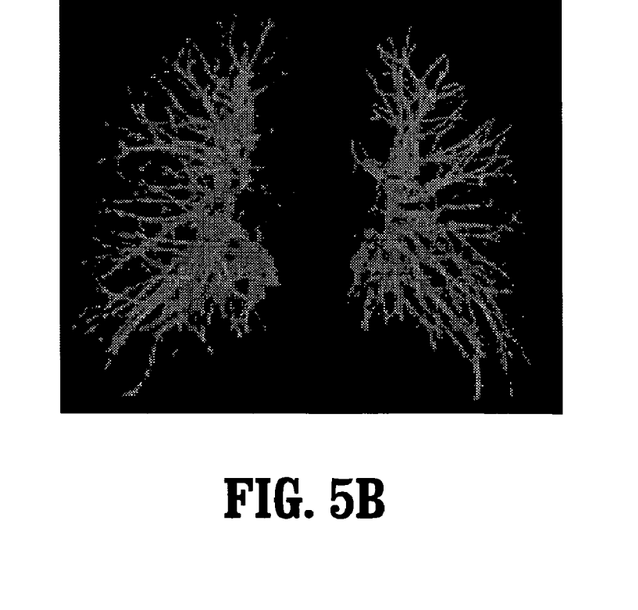
FIG. 5B is a computed arterial tree model using the segmented arterial tree of FIG. 4B.
Figure 6A:
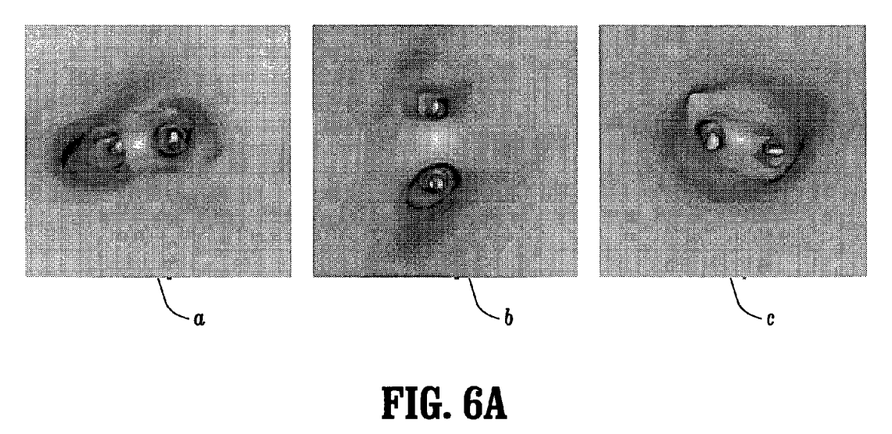
FIG. 6A is an internal view of the computed bronchial tree model of FIG. 5A.
Figure 6B:
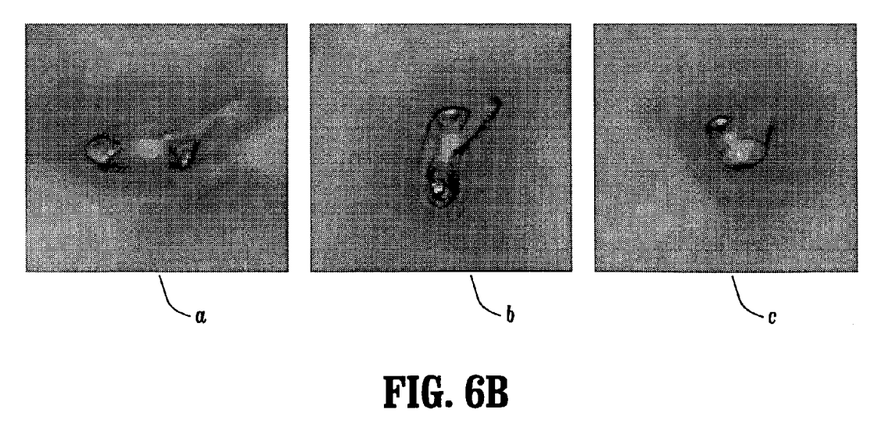
FIG. 6B is an internal view of the computed arterial tree model of FIG. 5B.

Once the airway and arterial trees are in a tree structure format as shown in FIGS. 5A and 5B, an automatic comparison of their branch points and/or branches is performed (step 240). One technique for comparing and/or matching branches is described in Tschirren J., Palagyi K., Reinhardt J. M., et al., "Segmentation, skeletonization, and branchpoint matching. A fully automated quantitative evaluation of human intrathoractic airway trees", Fifth International Conference on Medical Imaging Computing and Computer Assisted Intervention, New York, N.Y., 2002, a copy of which is herein incorporated by reference. This technique may be used in accordance with the present invention. It is to be understood, however, that other techniques for matching branches can also be used with the present invention. Examples of internal views of airways (a, b, c) and arteries (a, b, c) that were matched are shown in FIGS. 6A and 6B respectively.

In another embodiment of the present invention, at step 240, individual bronchial and arterial paths to a target nodule can be matched in place of matching bronchial and arterial trees. For example, once an arterial tree model has been fitted to match extracted airways, tree branches ending 1 cm or less from the target nodule are searched. The branch with the shortest distance to the target nodule is chosen. In the event that two or more branches end within 1 cm of the target nodule, these will be stored for subsequent evaluation. Once a branch is selected, the path from the trachea is determined from the tree model by tracing a path back to the trachea.

In order to determine a matching arterial path, vessel paths that pass near the target nodule are searched to determine which path is the closest to the automatically extracted bronchial path, which is measured by computing the distance between the points on the two paths and taking the average thereof. Next, the following criteria is evaluated to determine whether the matching artery path is sufficient to serve as a surrogate for navigation: 1) the number of branch segments along the path, 2) the location of each branch, 3) the lengths of branches, and 4) the branch angles for the airway and arterial paths; this evaluation occurs for the portions of the path that lie within a given distance (e.g., 2 cm) of the target. Pathways will be considered as matching if the differences between the number of branches, branch angles, location and lengths of all branches are less than or equal to a threshold value. If the closest arterial pathway deviates more than the threshold from the bronchial pathway, then the next closest arterial pathway is evaluated to see if it meets the criteria for matching.

Figure 3:
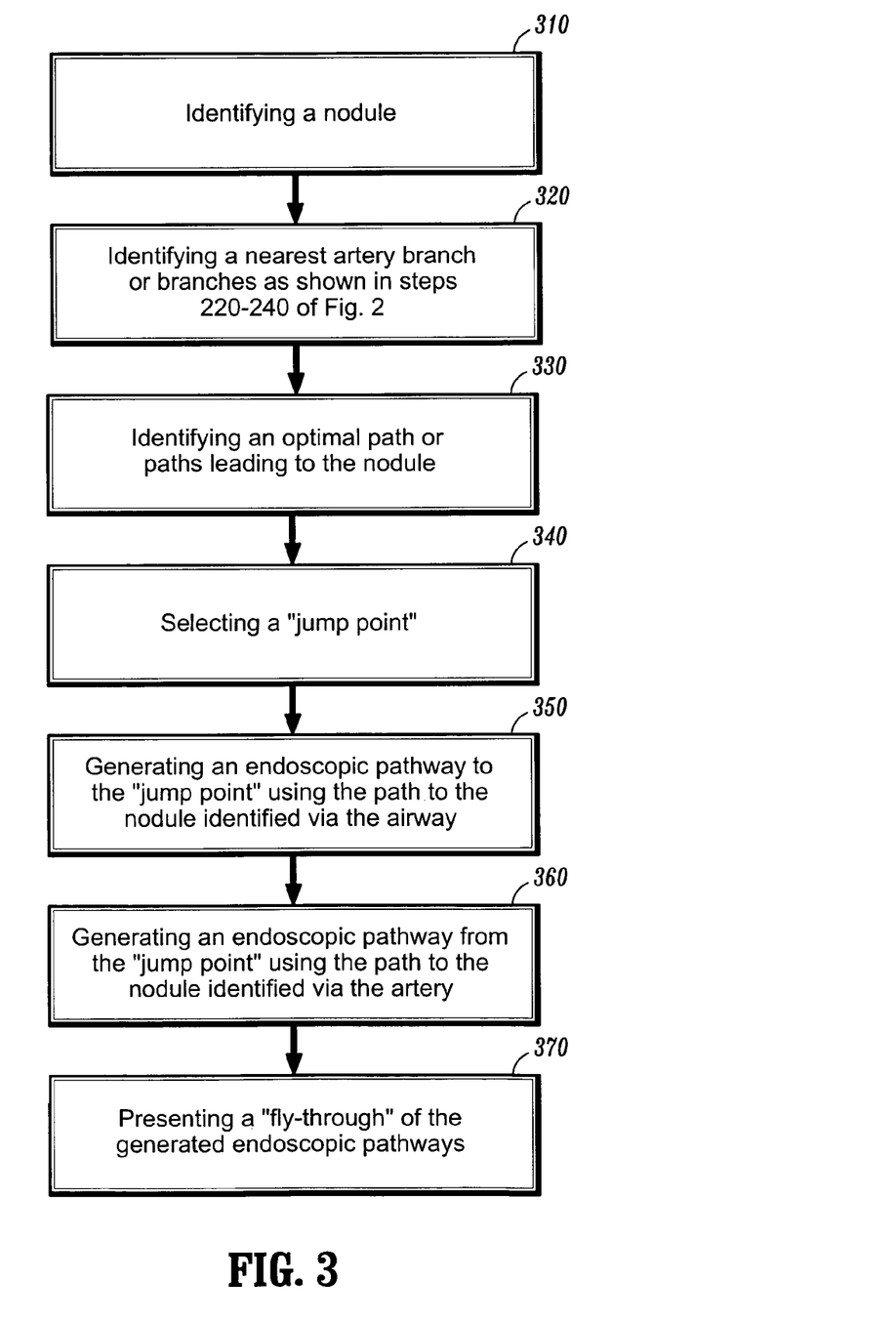
FIG. 3 is a flowchart illustrating a method for endoscopic path planning according to an exemplary embodiment of the present invention.

FIG. 3 is a flowchart showing an operation of a method for endoscopic path planning according to an exemplary embodiment of the present invention. More particularly, FIG. 3 illustrates a method for automatically deriving computer-generated virtual endoscopic pathways leading from airways to peripheral nodules using arteries as surrogate markers for the location of peripheral airways when they cannot be identified by CT scans.

As shown in FIG. 3, a medical expert such as a bronchoscopist identifies a target such as a nodule in a lung that they wish to biopsy (step 310). It is to be understood that the target can also be a focal abnormality such as a cancerous protrusion, non-cancerous protrusion, lesion, tumor, stenosis, mucus, or inflammation. After the bronchoscopist identifies the target nodule, the system identifies the artery branch or branches nearest to the target nodule by: 1) performing any of the steps or a combination of the steps of FIG. 2, or 2) using data previously stored, for example, in the memory 130 of the CPU 125 that was previously acquired while performing the steps of FIG. 2 (step 320). Step 320 may also include the step of identifying the matching airway path that corresponds to the artery path (discussed below in step 240).

An optimal arterial path (e.g., shortest path to the nodule) is then chosen from the paths in the computed arterial tree model (step 330). This may be accomplished, for example, using conventional automated path planning techniques that are used to identify an optimal airway or arterial path or paths leading to target nodules. In addition, manual path planning techniques may also be used in this step.

A "jump point" is subsequently selected (step 340). The "jump-point" is, for example, a location on the airway path near where the detectable airway tree ends, and its corresponding location on the arterial path. In other words, the "jump point" indicates where virtual bronchoscopic navigation (e.g., virtual navigation via the airways or bronchi) is no longer possible and where virtual angioscopic navigation (e.g., virtual navigation via blood vessels or arteries) will take over. The "jump point" can also be defined as a location within a selected area along or near the airway path prior to the end of the airway tree, in addition, the "jump point" can be located in a midpoint of any airway branch rather than at a bifurcation. An exemplary "jump point" is illustrated by a horizontal line in the area enclosed by a circle 730 in FIG. 7.

Figure 7:
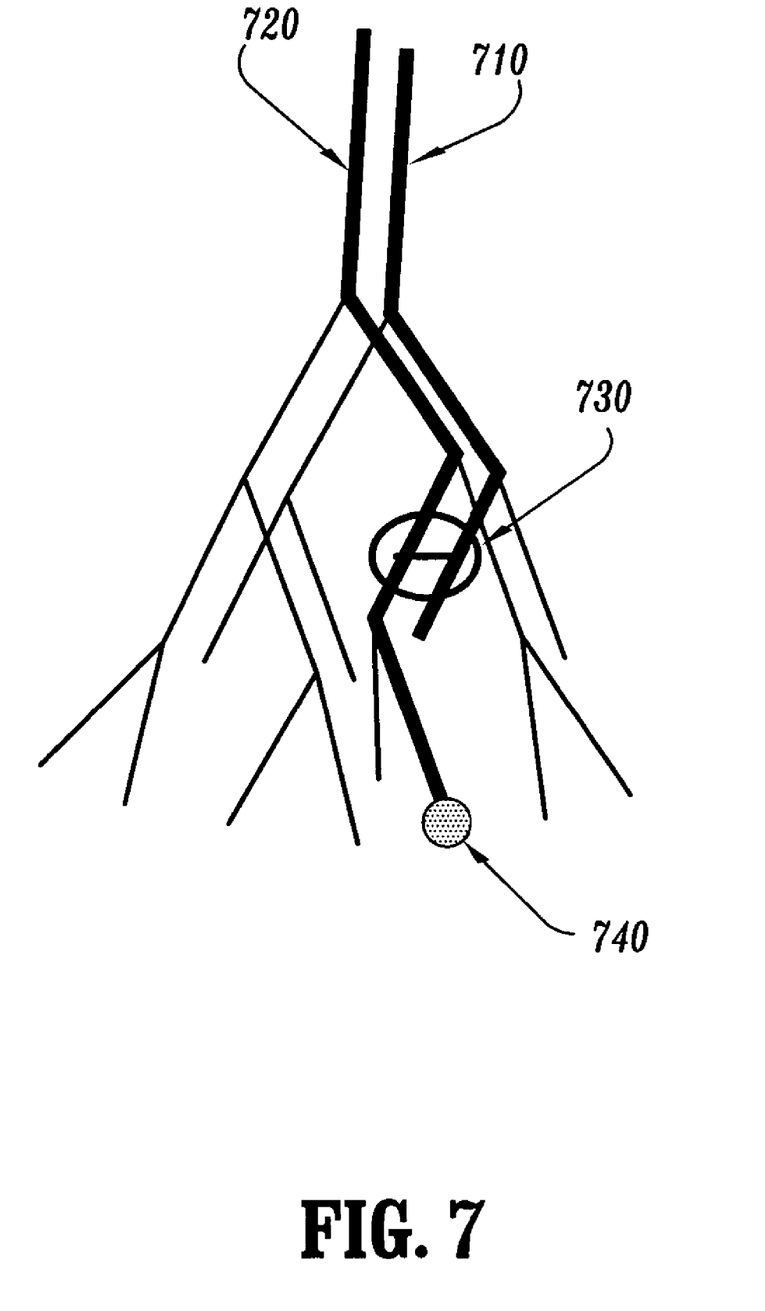
FIG. 7 is a schematic view of the matching bronchial and arterial tree models and endoscopic paths.

FIG. 7 also illustrates a bronchial sub-tree 710 leading toward a target nodule 740, and an arterial sub-tree 720 corresponding to the bronchial sub-tree 710 also leading to the target nodule 740. As shown in FIG. 7, the bronchial sub-tree 710 and the arterial sub-tree 720 demonstrate similar features, however, the arterial sub-tree 720 contains additional branches that are visible in the peripheral region (e.g., the additional branches are located beyond the limit or end of the bronchial sub-tree). Thus, once the path along the bronchial sub-tree 710 ends or the "jump point" is reached, a corresponding arterial sub-tree 720 is used to plot a path to the target nodule 740 in the peripheral region. In other words, the arterial path serves as a roadmap for the unseen airway path because the airway path is not visible due to, for example, the resolution of the CT scanner and partial volume effects.

After step 340, an endoscopic pathway is automatically generated beginning, for example, at a carina, or trachea and proceeding through the bronchial sub-tree 710 to the "jump point" (step 350). An endoscopic pathway is then automatically generated beginning from the "jump point" to the target nodule 740 (step 360). A "fly-through" (e.g., a virtual endoscopic movie) of the endoscopic pathways generated in steps 350 and 360 is then presented to a user, for example, of the virtual navigation terminal 115 (step 370).

Thus, according to the present invention as described above, a medical expert such as a bronchoscopist can plan an endoscopic path that allows the bronchoscopist to navigate from central airways of a lung to peripheral lung nodules despite the absence of identifiable peripheral airways in the lung. Accordingly, by employing the present invention a conventional virtual endoscopic system can be enhanced to create and/or augment a program associated with virtual navigation of a lung to improve the accuracy at which a bronchoscopist can plan a path to peripheral nodules for medical evaluation.

In another embodiment of the present invention, automatic arterial and bronchial tree matching is replaced by user selection. In this embodiment (shown in FIG. 8), a user selects a target nodule or another abnormality within the lungs (step 810). The selection is accomplished by using, for example, a mouse and clicking on the target nodule. Next, the user selects a location inside an artery leading to the target nodule and a location inside a matching bronchus (step 820). The selected locations are referred to as a "jump point". The PC 110 automatically determines which selection (e.g., the selection inside the artery and the selection inside the bronchus) corresponds to which structure by testing the Hounsfield value at the select point and/or points. The automatic determination exploits the fact that the insides of airways have lower Hounsfield values than the insides of arteries. Next, the user identifies an artery that passes near the nodule and leads to the "jump point" (step 830).

Figure 8:
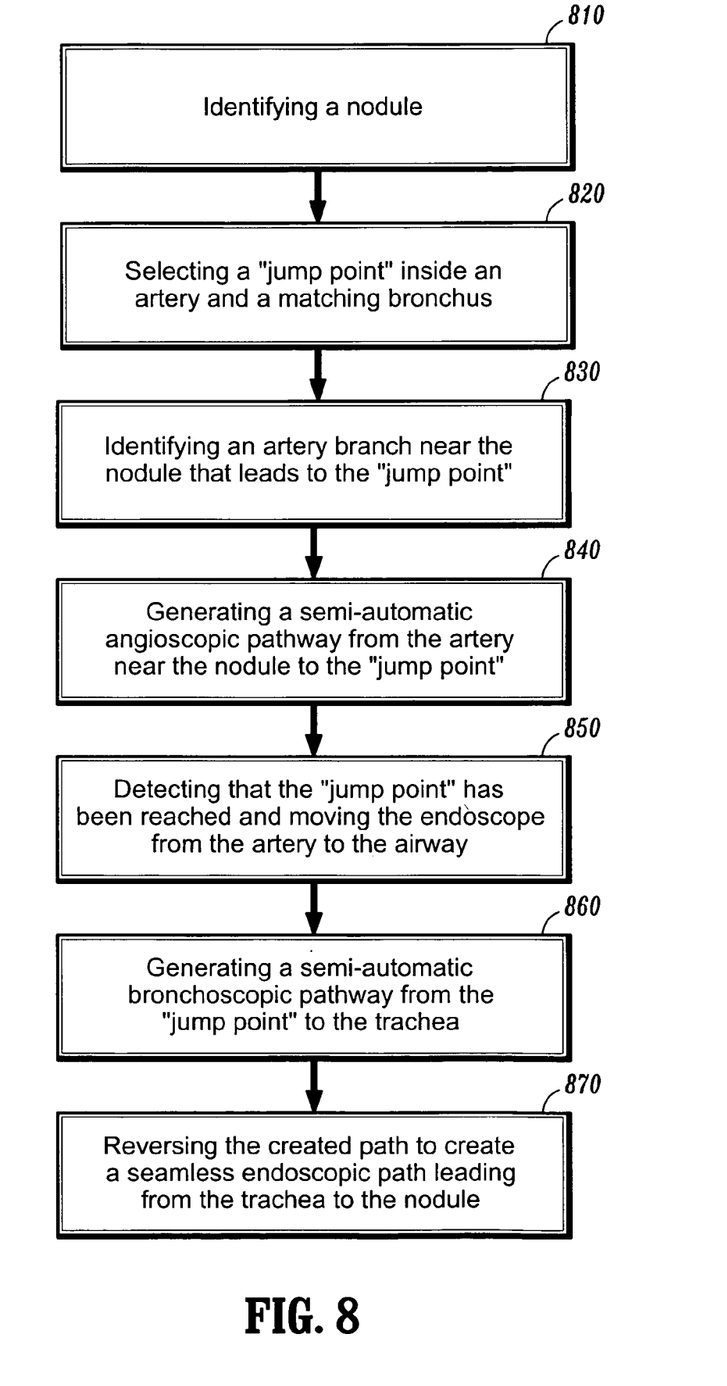
FIG. 8 is a flowchart illustrating another method for endoscopic path planning according to an exemplary embodiment of the present invention.

Beginning at the artery near the nodule, an angioscopic pathway is semi-automatically generated, leading through the artery until it reaches the "jump point" (step 840). The PC 110 automatically adjusts the endoscopic viewing parameters for angioscopy by setting voxel values with a density value equal to water as transparent, and voxel values with a density value equal to air as opaque. The pathway direction is automatically determined by calculating the longest ray that remains inside the artery. As needed, the user may interactively adjust the rendering values in order to close up gaps or open up a pathway. In addition, the user may adjust the travel direction by steering the mouse to the left or right. However because the direction of travel is toward the heart, from smaller arterial branches into larger arterial branches, there are no bifurcations and thus a decision as to which branch should be taken is not typically necessary.

The PC 110 then automatically determines when the path has reached the "jump point" within the artery by testing whether the current endoscopic path location is within a threshold distance of the jump point (e.g., within 5 mm) (step 850). Then the endoscope is automatically repositioned to the matching location in the bronchus. The initial viewing vector for the endoscope is the same as it was in the artery immediately prior to the "jump point". The rendering parameters are automatically adjusted for bronchoscopic viewing by inverting them, so that voxel values equal to air are rendered as transparent, and voxel values equal to tissue (i.e. the walls of the airways) are rendered as opaque.

A bronchoscope path leading from the "jump point" to the trachea is then automatically or semi-automatically created (step 860). As with the angioscopic path, the direction of travel is taken as the longest ray that remains inside the bronchus. Semi-automatic corrections to the direction may be indicated by the user; however, because the direction of travel is still retrograde, there are no bifurcation decisions and the path may usually be created automatically. Subsequently, the angioscopic path leading from the nodule to the "jump point" and the bronchoscopic path leading from the "jump point" to the trachea are reversed (step 870). Thus, a seamless path from the trachea to the nodule is created, showing a bronchoscopist a path that leads all the way to the target nodule.

In another embodiment of the present invention, endoscopic path planning can be used in conjunction with a bronchoscopy. In this embodiment, after a bronchoscope has been inserted into a trachea, a CT image set is acquired in order to assess where the tip of the bronchoscope is in relation to where it should be. This is accomplished by automatically and in real-time registering the CT images acquired during the bronchoscopy with the CT images obtained during endoscopic path planning.

In order to automatically and in real-time register the CT images acquired during the bronchoscopy with the CT images obtained during endoscopic path planning, a modified method for matching nodule locations in two CT datasets acquired at different times as disclosed in Shen H., Fan L., Qian J., et al.: "Real-time and automatic matching of pulmonary nodules in follow-up multi-slice CT studies", Proceedings of the International Conference on Diagnostic Imaging and Analysis, Shanghai, 2002, a copy of which is herein incorporated by reference, is used. The method of Shen et al. begins with an approximate global linear alignment of the two CT datasets based on the lung area in each axial, coronal, and sagittal slice. Given the location of a nodule in one CT dataset, the approximate alignment gives an initial search position in the other dataset. Surface maps of a binarized volume centered on the nodule position and the start position in the other dataset are computed, and then searched locally for the most similar match or matches.

By applying the technique of Shen et al. to any region of high contrast within the lungs, the location of the bronchoscope in a current CT image in relation to the planned endoscopic path is determined. In addition, by applying the technique of Shen et al. to register the bronchoscope tip position, images that are acquired with the bronchoscope can be instantaneously transmitted to the CPU 125 or the virtual navigation terminal 115 for viewing. Thus, by precisely matching image sections demonstrating the bronchoscope tip with previously acquired axial, sagittal and coronal images at the same level, which are labeled to identify the pertinent airways and vessels, allows bronchoscopists to determine the accuracy of their position in real-time to ensure that they are properly following the previously planned endoscopic path. Accordingly, real-time feedback of the current bronchoscope position in relation to the planned endoscopic path will enable a bronchoscopist to be sure that they are in the proper endoscopic location, or it will allow them to reposition the bronchoscope to the correct location in a timely manner.

It is to be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be straightforwardly implemented without departing from the spirit and scope of the present invention. It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A system for endoscopic path planning, comprising:
a memory device for storing a program;
a processor in communication with the memory device, the processor operative with the program to:
receive an image of a lung, wherein the image includes airways and arteries, and wherein certain peripheral airways are not visible in the image, but peripheral arteries corresponding to the non-visible peripheral airways are visible in the image;
identify a target in an image of a lung, wherein the target is located near a non-visible peripheral airway; and
automatically generate an endoscopic path to the target, wherein the endoscopic path follows a visible airway that leads to the non-visible peripheral airway, and then, follows a path computed by the processor based on coordinates of the non-visible peripheral airway's nearest matching peripheral artery to the target,
wherein the endoscopic path is inside the visible airway that leads to the non-visible peripheral airway and the non-visible peripheral airway that leads to the target.

2. The system of claim 1, wherein when the system is used to perform a bronchoscopy, the processor is further operative with the program to:
receive an image that identifies a location of a tip of a bronchoscope that has been inserted into the lung;
register the image with a corresponding image from the endoscopic path; and
determine where the tip of the bronchoscope is located in relation to where it should be located in the endoscopic path.

3. The system of claim 2, wherein the processor is further operative with the program to:
cause a user to reposition the tip of the bronchoscope to match where it should be located in the endoscopic path.

4. The system of claim 1, wherein the target comprises a nodule, cancerous protrusion, non-cancerous protrusion, lesion, tumor, or stenosis.

5. The system of claim 1, wherein the image is received from a device employing a computed tomographic (CT), helical CT, x-ray, positron emission tomographic, fluoroscopic, ultrasound, or magnetic resonance (MR) imaging technique.

6. The system of claim 1, wherein the processor is further operative with the program when identifying the target to:
select the target.

7. The system of claim 1, wherein the processor is further operative with the program when generating an endoscopic path to the target to:
segment airways and arteries in the lung;
compute an airway tree of the segmented airways and an artery tree of the segmented arteries;
match the computed airway and artery trees to each other;
use the matched trees to find the non-visible peripheral airway's nearest matching peripheral artery; and
select a jump point where the endoscopic path switches from following the visible airway to following the path computed based on coordinates of the nearest matching peripheral artery.

8. The system of claim 7, wherein the jump point is near an end of the visible airway.

9. The system of claim 7, wherein the jump point is at a midpoint of the visible airway.

10. The system of claim 1, wherein the processor is further operative with the program to:
display the endoscopic path.

11. A system for endoscopic path planning, comprising:
means for receiving an image of a lung, wherein the image includes airways and arteries, and wherein certain peripheral airways are not visible in the image, but peripheral arteries corresponding to the non-visible peripheral airways are visible in the image;
means for identifying a target in an image of a lung, wherein the target is located near a non-visible peripheral airway; and
means for automatically generating an endoscopic path to the target, wherein the endoscopic path follows a visible airway that leads to the non-visible peripheral airway, and then, follows a path computed by a machine based on coordinates of the non-visible peripheral airway's nearest matching peripheral artery to the target,
wherein the endoscopic path is inside the visible airway that leads to the non-visible peripheral airway and the non-visible peripheral airway that leads to the target.

* * * * *